(12) United States Patent
Okamoto

(10) Patent No.: US 6,977,147 B2
(45) Date of Patent: Dec. 20, 2005

(54) METHOD OF SCREENING THERAPEUTIC OR PREVENTATIVE AGENTS FOR SQUAMOUS EPITHELIAL CELL CARCINOMA

(75) Inventor: Tetsuji Okamoto, Hiroshima (JP)

(73) Assignee: Zeria Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/953,562

(22) Filed: Sep. 17, 2001

(65) Prior Publication Data
US 2003/0096241 A1 May 22, 2003

(30) Foreign Application Priority Data
Mar. 22, 2001 (JP) ........................................ 2001-083352

(51) Int. Cl.$^7$ ........................... C12Q 1/68; C12P 19/34; C07H 21/04; C12N 5/10
(52) U.S. Cl. ........................... 435/6; 435/91.2; 435/325; 536/23.5
(58) Field of Search ........................... 435/6, 91.2, 325, 435/7.1; 536/23.5; 530/350; 436/63; 424/9.2; 514/50

(56) References Cited

PUBLICATIONS

Grem, J.L. 5–fluorouracil: forty–plus and still ticking. A review of its preclinical and clinical development. Investigational New Drugs 18(4):299–313 (Nov. 2000).*
Yee, C.J. et al. Analysis of fibroblast growth factor receptor 3 S249C mutation in cervical carcinoma. Journal of the National Cancer Institute 92(22):1848–1849 (Nov. 2000).*
van Rhijn, B.W.G. et al. The fibroblast growth factor receptor 3 (FGFR3) mutation is a strong indicator of superficial bladder cancer with low recurrence rate. Cancer Research 61(4):1265–1268 (Feb. 2001).*
M. Chesi et al.; "Frequent Translocation T(4;14) (P16.3;Q32.3) in Multiple Myeloma is Associated with Increased Expression and Activating Mutations of Fibroblast Growth Factor Receptor 3"; Nature Genetics; vol. 16; pp. 260–264; 1997.
D. Cappellen et al.; "Frequent Activating Mutations of FGFR3 in Human Bladder and Cervix Carcinomas"; Nature Genetics; vol. 23; pp. 18–20; 1999.
J. H. Jang et al.; "Novel Transcripts of Fibroblast Growth Factor Receptor 3 Reveal Aberrant Splicing and Activation of Cryptic Splice Sequences in Colorectal Cancer", Cancer Research 2000; 60(15); pp. 4049–4052.
D. Gospodarowicz et al.; "Purification of a Growth Factor for Ovarian Cells from Bovine Pituitary Glands"; Proc. Natl. Acad. Sci. USA; vol. 71; no. 6; pp. 2295–2299; 1974.
T. Nishimura et al.; "Identification of a Novel FGF, FGF–21, Preferentially Expressed in the Liver"; Biochem. Biophys. Acta.;1492; pp. 203–206; 2000.

(Continued)

Primary Examiner—Diana B. Johannsen
(74) Attorney, Agent, or Firm—Armstrong, Kratz, Quintos, Hanson & Brooks, LLP

(57) ABSTRACT

There is provided a method of testing squamous epithelial cells and a method of screening therapeutic agents for squamous cell carcinoma. That the base guanine at position 2128 (exon 17) of the FGFR3 gene is mutated to thymine in the cells of squamous cell carcinoma, or that the cells of squamous cell carcinoma produce an FGFR3 protein in which the amino acid glycine at position 697 is mutated to cysteine is utilized to facilitate the diagnosis and treatment of squamous cell carcinoma.

3 Claims, 7 Drawing Sheets

PUBLICATIONS

D. Johnson et al.; "Structural and Functional Diversity in the FGF Receptor Multigene Family"; Advances in Cancer–Res.; 60:1; pp. 1–41; 1993.

J. Adnane et al.; "Bek and Flg, Two Receptors to Member of Te Fgf Family, are Amplified in Subsets of Human Breast Cancers"; Oncogene; vol. 6; pp. 659–663; 1991.

M. Muenke et al.; "Fibroblast–Growth–Factor Receptor Mutations in Human Skeletal Disorders"; Trend in Genetics; vol. 11; pp. 308–313; 1995.

E. W. Jabs; "Jackson–Weiss and Crouzon Syndromes are Allelic with Mutations in Fibroblast Growth Factor Receptor 2"; Nature Genetics; vol. 3; pp. 275–279; 1994.

X Li et al.; "Effect on Splicing of a Silent FGFR2 Mutation in Crouzon Syndrome"; vol. 9; pp. 232–233; 1995.

M. Muenke et al.; "A Common Mutation in the Fibroblast Growth Factor Receptor 1 Gene in Pfeiffer Syndrome"; vol. 8; pp. 269–274; 1994.

P. Rutland et al.; "Identical Mutations in the FGFR2 Gene Cause Both Pfeiffer and Crouzon Syndrome Phenotypes"; vol. 9; pp. 173–176; 1995.

E. Lajeunie et al.; "FGFR2 Mutations in Pfeiffer Syndrome"; Nature Genetics; vol. 9; p. 108; 1995.

U. Schell et al.; "Mutations in FGFR1 and FGFR2 Cause Familial and Sporadic Pfeiffer Syndrome"; vol. 4; pp. 323–328; 1995.

A. Wilkie et al.; "Apert Syndrome Results from Localized Mutations of FGFR2 and is Allelic with Crouzon Syndrome"; Nature Genetics; vol. 9; pp. 165–172; 1995.

R. Shiang et al.; "Mutations in the Transmembrane Domain of FGFR3 Cause the Most Common Genetic Form of Dwarfism, Achondroplasia"; Cell; vol. 78; pp. 335–342; 1994.

F. Rousseau et al.; "Mutations in the Gene Encoding Fibroblast Growth Factor Receptor–3 in Achondroplasia"; Nature; vol. 371; pp. 252–254; 1994.

P. Tavormina et al.; "Thanatophoric Dysplasia (Types I and II) Caused by Distinct Mutations in Fibroblast Growth Factor Receptor 3"; Nature Genetics; vol. 9; pp. 321–328; 1995.

G. Meyers et al.; "Fibroblast Growth Factor Receptor 3 (FGFR3) Transmembrane Mutation in Crouzon Syndrome with Acanthosis Nigricans"; Nature Genetics; vol. 11; pp. 462–464; 1995.

I. Mason et al.; "The Ins and Outs of Fibroblast Growth Factors"; Cell; vol. 78; pp. 547–552; 1994.

C. H. Heldin; "Dimerization of Cell Surface Receptors in Signal Transduction"; Cell. vol. 80; pp. 213–223; 1995.

D. M. Ornitz; FGFs, Heparan Sulfate and FGFRs: Complex Interactions Essential for Development; Bio Essays; vol. 22; pp. 108–112; 2000.

A. Isacchi et al.; "Complete Sequence of a Human Receptor for Acidic and Basic Fibroblast Growth Factors"; Nucleric Acids Research; vol. 18; p. 1906; 1990.

D. Johnson et al.; "Diverse Forms of a Receptor for Acidic and Basic Fibroblast Growth Factors"; Molecular and Cellular Biology; vol. 10; pp. 4728–4736; 1990.

C. Dionne et al.; "Cloning and Expression of Two Distinct High–Affinity Receptors Cross–Reacting with Acidic and Basic Fibroblast Growth Factors"; The EMBO Journal; vol. 9; pp. 2685–2692; 1990.

E. Houssaint et al.; "Related Fibroblast Growth Factor Receptor Genes Exist in the Human Genome"; Pro. Natl. Acad. Sci. USA; vol. 87; pp. 8180–8184, 1990.

K. Keegan et al.; "Isolation of an Additional Member of the Fibroblast Growth Factor Receptor Family, FGFR–3"; Proc. Natl. Acad. Sci. USA; vol. 88; pp. 1095–1099; 1991.

L. Thompson et al.; "A Gene Encoding a Fibroblast Growth Factor Receptor Isolated from the Huntington Disease Gene Region of Human Chromosome 4"; Genomics; vol. 1; pp. 1133–1142; 1991.

J. Partanen et al.; "FGFR–4, A Novel Acidic Fibroblast Growth Factor Receptor with a Distinct Expression Pattern"; The EMBO Journal; vol. 10, no. 6; pp. 1347–1354; 1991.

S. Vainikka et al.; "Fibroblast Growth Factor Receptor–4 Shows Novel Features in Genomic Structure, Ligand Binding and Signal Transduction"; The EMBO Journal; vol. 11, No. 12; pp. 4273–4280; 1992.

M. Jaye et al.; "Fibroblast Growth Factor Receptor Tyrosine Kinases; Molecular Analysis and Signal Transduction"; Biochem–Biophys–Acta.; vol. 1135; pp. 185–199; 1992.

D. Ornitz et al.; "Receptor Specificity of the Fibroblast Growth Factor Family"; Journal of Biological Chemistry; vol. 271, No. 25; pp. 15292–15297; 1996.

A. Avivi et al.; "A Novel Form of FGF Receptor–3 Using an Alternative Exon in the Immunoglobulin Domain III"; FEBS Letter; vol. 330; pp. 249–252; 1993.

B. Murgue et al.; "Identification of a Novel Variant Form of Fibroblast Growth Factor Receptor 3 (FGFR3IIIb) in Human Colonic Epithelium"; vol. 54; pp. 5206–5211; 1994.

D. Johnson et al.; "The Human Fibroblast Growth Factor Receptor Genes; A Common Sructural Arrangement Underlies the Mechanisms for Generating Receptor Forms that Differ in Their Third Immunoglobulin Domain"; Molecular and Cellular Biology; vol. 11; pp. 4627–4634; 1991.

S. Werner et al.; "Differential Splicing in the Extracellular Region of Fibroblast Growth Factor Receptor 1 Generates Receptor Variants with Different Ligand–Binding Specificities"; Molecular and Cellular Biology; vol. 12; pp. 82–88; 1992.

E. Shi et al.; "Control of Fibroblast Growth Factor Receptor Kinase Signal Transduction by Heterodimerization of Combinatorial Splice Variants"; Molecular and Cellular Biology; vol. 13; pp. 3907–3918; 1993.

A. Chellaiah et al.; "Fibroblast Growth Factor Receptor (FGFR) 3"; The Journal of Biological Chemistry; vol. 269; pp. 11620–11627; 1994.

M. Webster et al.; "FGFR Activation in Skeletal Disorders: Too Much of a Good Thing"; Trends in Genetics; vol. 13; pp. 178–182; 1997.

R. J. Gorlin; "Fibroblast Growth Factors, Their Receptors and Receptor Disorders"; Journal of Cranio–Maxillofacial Surgery; vol. 25; pp. 69–79;1997.

C. Drugan et al.; "Fibroblast Growth Factor Receptor Expression Reflects Cellular Differentiation in Human Oral Squamous Carcinoma Cell Lines"; Carcinogenesis; vol. 19; pp. 1153–1156; 1998.

Y. Myoken et al.; "Immunocytochemical Localization of Fibroblast Growth Factor–1 (FGF–1) and FGF–2 in Oral Squamous Cell Carcinoma (SCC)"; Journal Oral Pathol Med.; vol. 23; pp. 451–456; 1994.

W. Reardon et al.; "Mutations in the Fibroblast Growth Factor Receptor 2 Gene Cause Crouzon Syndrome"; Nature Genetics; vol. 8; pp. 98–103; 1994.

* cited by examiner

SEQ ID NO.26

A: ─────
T: ━━━━
C: ─ ─ ─
G: ─·─·─

BEFORE TREATMENT

C C C T G C A T C C

SEQ ID NO.27

AFTER TREATMENT

C C C G G C A T C C

SEQUENCE LISTING

<160> NUMBER OF SEQ ID NOS: 27

<210> SEQ ID NO 1
<211> LENGTH: 29
<212> TYPE: DNA

-continued

```
<213> ORGANISM: Artificial Sequence
<220> FEATURE:
<223> OTHER INFORMATION: Upstream primer

<400> SEQUENCE: 1
tggaattcaa cgcgtccatg agctccaac                                    29

<210> SEQ ID NO 2
<211> LENGTH: 27
<212> TYPE: DNA
<213> ORGANISM: Artificial Sequence
<220> FEATURE:
<223> OTHER INFORMATION: Downstream primer

<400> SEQUENCE: 2
cagaattcct tcacgtccgc gagcccc                                      27

<210> SEQ ID NO 3
<211> LENGTH: 19
<212> TYPE: DNA
<213> ORGANISM: Artificial Sequence
<220> FEATURE:
<223> OTHER INFORMATION: FGFR3 mutagenic oligonucleotide

<400> SEQUENCE: 3
ccgtacccct gcatccctg                                               19

<210> SEQ ID NO 4
<211> LENGTH: 19
<212> TYPE: DNA
<213> ORGANISM: Artificial Sequence
<220> FEATURE:
<223> OTHER INFORMATION: Exon 10 upstream primer

<400> SEQUENCE: 4
ctagactcac tggcgttac                                               19

<210> SEQ ID NO 5
<211> LENGTH: 19
<212> TYPE: DNA
<213> ORGANISM: Artificial Sequence
<220> FEATURE:
<223> OTHER INFORMATION: Exon 10 downstream primer

<400> SEQUENCE: 5
gcagctcaga acctggtat                                               19

<210> SEQ ID NO 6
<211> LENGTH: 19
<212> TYPE: DNA
<213> ORGANISM: Artificial Sequence
<220> FEATURE:
<223> OTHER INFORMATION: Exon 11 upstream primer

<400> SEQUENCE: 6
cctgctgacc caagcaggt                                               19

<210> SEQ ID NO 7
<211> LENGTH: 19
<212> TYPE: DNA
<213> ORGANISM: Artificial Sequence
<220> FEATURE:
<223> OTHER INFORMATION: Exon 11 downstream primer

<400> SEQUENCE: 7
cctacagcca acgctggcc                                               19
```

```
<210> SEQ ID NO 8
<211> LENGTH: 20
<212> TYPE: DNA
<213> ORGANISM: Artificial Sequence
<220> FEATURE:
<223> OTHER INFORMATION: Exon 12 upstream primer

<400> SEQUENCE: 8
ccttacgaac agtctgtagg                                               20

<210> SEQ ID NO 9
<211> LENGTH: 19
<212> TYPE: DNA
<213> ORGANISM: Artificial Sequence
<220> FEATURE:
<223> OTHER INFORMATION: Exon 12 downstream primer

<400> SEQUENCE: 9
catcgtctgt gcacggagc                                                19

<210> SEQ ID NO 10
<211> LENGTH: 20
<212> TYPE: DNA
<213> ORGANISM: Artificial Sequence
<220> FEATURE:
<223> OTHER INFORMATION: Exon 13 upstream primer

<400> SEQUENCE: 10
cgctccgtgc acagacgatg                                               20

<210> SEQ ID NO 11
<211> LENGTH: 19
<212> TYPE: DNA
<213> ORGANISM: Artificial Sequence
<220> FEATURE:
<223> OTHER INFORMATION: Exon 13 downstream primer

<400> SEQUENCE: 11
cctcagacgg gctgccagg                                                19

<210> SEQ ID NO 12
<211> LENGTH: 18
<212> TYPE: DNA
<213> ORGANISM: Artificial Sequence
<220> FEATURE:
<223> OTHER INFORMATION: Exon 14 upstream primer

<400> SEQUENCE: 12
gtaggtgcgg tagcggcg                                                 18

<210> SEQ ID NO 13
<211> LENGTH: 18
<212> TYPE: DNA
<213> ORGANISM: Artificial Sequence
<220> FEATURE:
<223> OTHER INFORMATION: Exon 14 downstream primer

<400> SEQUENCE: 13
ctcccagcat ctcagggc                                                 18

<210> SEQ ID NO 14
<211> LENGTH: 19
<212> TYPE: DNA
<213> ORGANISM: Artificial Sequence
<220> FEATURE:
```

```
<223> OTHER INFORMATION: Exon 15 upstream primer

<400> SEQUENCE: 14
tgccctgaga tgctgggag                                               19

<210> SEQ ID NO 15
<211> LENGTH: 19
<212> TYPE: DNA
<213> ORGANISM: Artificial Sequence
<220> FEATURE:
<223> OTHER INFORMATION: Exon 15 downstream primer

<400> SEQUENCE: 15
gctcacgttg gttgtcttc                                               19

<210> SEQ ID NO 16
<211> LENGTH: 19
<212> TYPE: DNA
<213> ORGANISM: Artificial Sequence
<220> FEATURE:
<223> OTHER INFORMATION: Exon 16 upstream primer

<400> SEQUENCE: 16
catgccagta ggacgcctg                                               19

<210> SEQ ID NO 17
<211> LENGTH: 19
<212> TYPE: DNA
<213> ORGANISM: Artificial Sequence
<220> FEATURE:
<223> OTHER INFORMATION: Exon 16 downstream primer

<400> SEQUENCE: 17
gctgtcctga gactcccag                                               19

<210> SEQ ID NO 18
<211> LENGTH: 19
<212> TYPE: DNA
<213> ORGANISM: Artificial Sequence
<220> FEATURE:
<223> OTHER INFORMATION: Exon 17 upstream primer

<400> SEQUENCE: 18
gaccgagtct acactcacc                                               19

<210> SEQ ID NO 19
<211> LENGTH: 19
<212> TYPE: DNA
<213> ORGANISM: Artificial Sequence
<220> FEATURE:
<223> OTHER INFORMATION: Exon 17 downstream primer

<400> SEQUENCE: 19
gacaggtcca ggtactcgt                                               19

<210> SEQ ID NO 20
<211> LENGTH: 19
<212> TYPE: DNA
<213> ORGANISM: Artificial Sequence
<220> FEATURE:
<223> OTHER INFORMATION: Exon 18 upstream primer

<400> SEQUENCE: 20
gactcactcc tgagcgccc                                               19
```

-continued

```
<210> SEQ ID NO 21
<211> LENGTH: 19
<212> TYPE: DNA
<213> ORGANISM: Artificial Sequence
<220> FEATURE:
<223> OTHER INFORMATION: Exon 18 downstream primer

<400> SEQUENCE: 21
cgcacagcca cctctgtgc                                              19

<210> SEQ ID NO 22
<211> LENGTH: 19
<212> TYPE: DNA
<213> ORGANISM: Artificial Sequence
<220> FEATURE:
<223> OTHER INFORMATION: Exon 19 upstream primer

<400> SEQUENCE: 22
tcaccccgcc tcccgccag                                              19

<210> SEQ ID NO 23
<211> LENGTH: 20
<212> TYPE: DNA
<213> ORGANISM: Artificial Sequence
<220> FEATURE:
<223> OTHER INFORMATION: Exon 19 downstream primer

<400> SEQUENCE: 23
ccagtggccc ttcacgtccg                                             20

<210> SEQ ID NO 24
<211> LENGTH: 24
<212> TYPE: DNA
<213> ORGANISM: homo sapiens

<400> SEQUENCE: 24
ctcccgtacc ccggcatccc tgtg                                        24

<210> SEQ ID NO 25
<211> LENGTH: 24
<212> TYPE: DNA
<213> ORGANISM: homo sapiens

<400> SEQUENCE: 25
ctcccgtacc cctgcatccc tgtg                                        24

<210> SEQ ID NO 26
<211> LENGTH: 10
<212> TYPE: DNA
<213> ORGANISM: homo sapiens

<400> SEQUENCE: 26
ccctgcatcc                                                        10

<210> SEQ ID NO 27
<211> LENGTH: 10
<212> TYPE: DNA
<213> ORGANISM: homo sapiens

<400> SEQUENCE: 27
cccggcatcc                                                        10
```

METHOD OF SCREENING THERAPEUTIC OR PREVENTATIVE AGENTS FOR SQUAMOUS EPITHELIAL CELL CARCINOMA

BACKGROUND OF THE INVENTION (1) Field of the Invention

The present invention relates to a method of testing squamous epithelial cells. The present invention also relates to a method of screening therapeutic agents for squamous cell carcinoma.

(2) Description of the Related Art

Since the discovery of a basic fibroblast growth factor (FGF-2) as a growth factor for fibroblasts in the early 1970's[1], the fibloblast growth factor (FGF) family that is encoded by 21 different genes has been elucidated up to now[2]. The activity of FGF is mediated by a high-affinity FGF receptor (FGFR) on the cell surface, and FGF has a structure composed of two or three extracellular immunoglobulin-like loop structures (1 g), a transmembrane domain, and, within the cell, a tyrosine kinase region divided into two parts[3]–[5]. It has been believed that FGFR, when bound to FGF in the presence of heparin or heparan sulfate proteoglycan, forms a dimer, which self-phosphorylates the tyrosine residue of the receptor or reciprocally phosphorylates each other, and transduces signals of cell growth, differentiation, and the like[6]–[8].

As the genes encoding FGFR, four types of genes have been identified[17] such as FGFR1[9]–[11], FGFR2[11],[12], FGFR3[13],[14], and FGFR4[15],[16]. Furthermore, it is known that, due to differences in selective splicing of exons encoding the immunoglobulin-like region (IgIII) corresponding to the extracellular ligand binding site, there are two types of splicing variants for each of FGFR1, FGFR,2, and FGFR3[18],[19], and a total of seven types of FGFR are known. Each FGFR has different binding ability[17],[20]–[24].

Recently, it was shown that anomalous FGFR causes various congenital skeletal and chondral dysplasia. It is reported that an anomalous FGFR1 gene causes Pfeiffer syndrome, an anomalous FGFR2 causes Crouzon syndrome, Jackson-Weiss syndrome, Pfeiffer syndrome, Apert syndrome and the like, an anomalous FGFR3 causes achondrogenesis and chondral hypoplasia, Crouzon syndrome complicated by acanthosis nigricans, thanatopholic dysplasia (type 1 and 2), FGFR3-related coronal synostosis syndrome, and the like[25],[26].

For example, mutations or Cys342Tyr, Ser354Cys, Tyr340His, etc. in FGFR2 for Crouzon syndrome[36]–[38] which is a lusus naturae complicated by coronal synostosis, Pro252Arg in FGFR1 for Pfeiffer syndrome[39]–[42], Ala344Gly in FGFR2 for Jackson-Weiss syndrome[37], and Ser252Trp and Pro253Arg in FGFR2 for Apert syndrome[43] are known. Furthermore, mutations of Gly380Arg in the FGFR3 transmembrane domain for achondroplasia[44],[45], Arg248Cys in FRFR3 for thanatophoric dysplasia type 1 (TDI)[46], Lys650Glu in FRFR3 for thanatophoric dysplasia type 2 (TDII)[46], Ala391Glu in FRFR3 for Crouzon syndrome complicated by acanthosis nigricans[47], and the like have been reported. In the analysis of FGFR molecules in these congenital diseases, permanent tyrosine-phosphorylating activity due to dimerization of receptors per se independent of ligands was observed, and the degree of tyrosine kinase activation of the receptor is thought to be correlated with the severity of the diseases[25].

Squamous cell carcinoma is a cancer on the stratified squamous epithelia that mainly cover the skin, the oral cavity, the esophagus, the vagina, the brohchus, and the like, and one of the most frequently seen skin cancers next to basal cell carcinoma. It is reported that any of the above four types exhibits FGFR in the cells of oral squamous cell carcinoma and in normal oral mucosa-derived epithelial cells, but their growth in the normal epithelial cells depends on FGF whereas in the cells of oral squamous cell carcinoma it does not depend on FGF[37],[38].

In gene diagnosis, the association of gene mutation with a disease is important. However, mutations of the FGFR gene have conventionally been reported on multiple myeloma, bladder cancer, cervical cancer or colon cancer (Nature Genetics, 260–264 (1997); Nature Genetics, 23: 18–20 (1999); and Cancer Research, 60(15): 4049–4052 (2000)), and no such reports have been made on squamous cell carcinoma. Thus, if the association of the FGFR gene with cancer for squamous cell carcinoma, in particular oral squamous cell carcinoma, it would be useful for the development of methods for diagnosing cancer diseases, and the screening and development of therapeutic agents thereof.

SUMMARY OF THE INVENTION

The present inventor has investigated exons 10–19 in the entire intracellular region of the FGFR3 gene derived from the tissue of oral squamous cell carcinoma, and mutation was suggested to occur only in exon 17 of the entire exons. In a further investigation of the base sequence of exon 17, it was found, the base at position 2128 of FGFR3 was guanine when the exon was derived from the normal cells, whereas it was thymine when it was derived from the cells of oral squamous cell carcinoma. This mutation corresponds to the replacement of the amino acid glycine at position 697 with cysteine (Gly697Cys).

On the other hand, the present inventor has also found that in a case of primary squamous cell carcinoma in the maxillary sinus, the mutation of the base at position 2128 of exon 17 of the FGFR3 gene from guanine to thymine was observed in DNA derived from untreated cancer tissues whereas no mutation was found in DNA derived from the cancer tissue of the same patient after treatment with an anti-cancer agent and radiation therapy.

The present inventor has also found that by investigating whether a candidate agent has an ability of inhibiting or preventing the mutation of the base at position 2128 of the FGFR3 gene, in the process of exploring therapeutic agents for squamous cell carcinoma, in particular oral squamous cell carcinoma, said therapeutic agents or preventive agents could be efficiently screened.

Based on the above findings, the present inventor has performed intensive research on the mutation and function of FGFR3 in squamous cell carcinoma, and thereby has completed the present invention.

Thus, the present invention is a method of testing squamous epithelial cells comprising judging that said cells can progress into squamous cell carcinoma when the base at position 2128 of the FGFR3 gene is mutated from guanine to thymine in said squamous epithelial cells isolated from the living body.

The present invention is also a method of screening therapeutic or preventive agents for squamous cell carcinoma, said method comprising applying a candidate therapeutic agent for squamous cell carcinoma to the cells of squamous cell carcinoma that have a mutation of the base at position 2128 (exon 17) of the FGFR3 gene from guanine to thymine or that produce the FGFR3 protein in which the amino acid at position 697 is mutated from glycine to cysteine, and then selecting said candidate agent by using as an index the fact that said base at said position 2128 of the FGFR3 gene of the squamous epithelial cells after application has been reverted to guanine or that the amino acid at position 697 of the produced FGFR3 protein has been reverted to glycine.

The present invention is also a pharmaceutical agent which is a therapeutic or preventive agent for squamous cell carcinoma obtained by the above screening method, said agent having a function of reverting the base at position 2128 (exon 17) of the FGFR3 gene which has been mutated from guanine to thymine to guanine in the living body.

In the above method of testing squamous cells, the method of screening a therapeutic or preventive agent, and the therapeutic or preventive agent, squamous cell carcinoma is preferably oral squamous cell carcinoma, and most preferably primary squamous cell carcinoma in the maxillary sinus.

DESCRIPTION OF THE PREFERRED EMBODIMENTS

Figure 1:
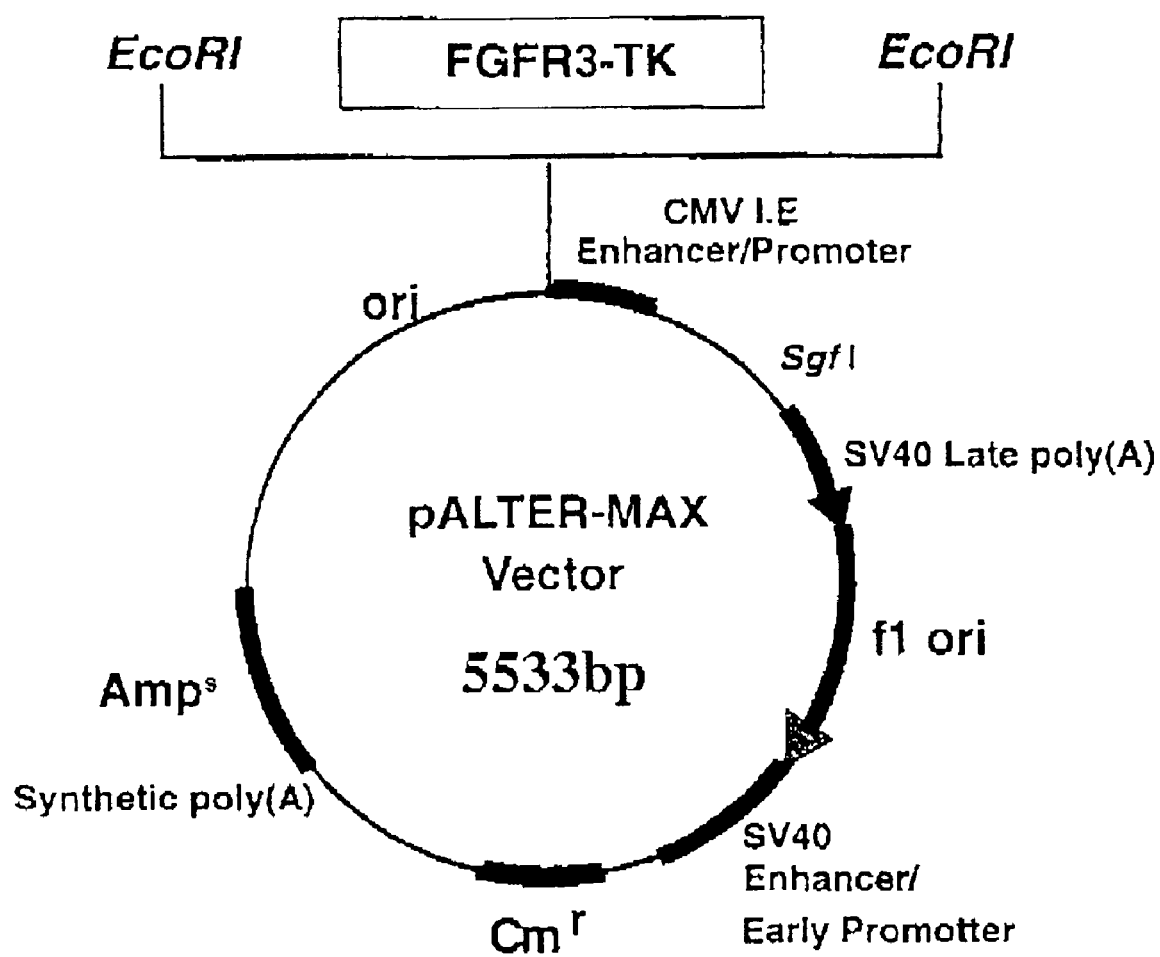
FIG. 1 shows the construction of the wild-type FGFR3 tyrosine kinase expression vector.

The present inventor has clarified that in oral squamous cell carcinoma the substitution of the amino acid glycine at position 697 of the FGFR3 protein with cysteine (Gly697Cys) based on the mutation of the base guanine at position 2128 of the FGFR3 gene to thymine (GGC→TGC, hereinafter this mutation will also be referred to as G2128T mutation) occurs at a high frequency (about 62%).

Since cysteine is an amino acid that has a —SH group and thereby forms a disulfide bond, that is deeply involved in protein confirmation, and that is important for the maintenance of the biological activity of proteins, the substitution of glycine with cysteine is believed to cause a ligand-independent dimerization of FGFR molecules, which results in the functional changes of the receptor including an increased amount of expressed FGFR3 and enhanced self-phosphorylation activity of FGFR3.

It is reported that squamous cell carcinoma has mutations in oncogenes and tumor suppressor genes such as p53, H-ras, MTS1 (p16), ING1 (p33) and the like. According to certain reports, the frequency of these gene mutations is about 10% in the oncogene H-ras[49)–51)], about 20% in the tumor suppressor gene MTS1[52),53)], about 10% in ING1[54),55)], and about 55% in P53[49)].

That C2128T mutation of FGFR3 in oral squamous cell carcinoma was observed at a high frequency of 44 of 71 cases, or about 62%, suggests a high possibility that the mutation could be used as a molecular target marker useful for the gene diagnosis of oral squamous cell carcinoma.

In an statistical analysis that was made for 71 cases studied herein on the relationship of the presence of mutation, the size of tumor (T), the presence of regional lymph node metastasis (N), the presence of late metastasis, the presence of bone resorption images in roentogenogram, etc. with clinical findings, no statistically significant differences were noted though cases with metastasis have shown a trend of high T values. This is believed to be due to the presence of mutations of FGFR3 at a high frequency of 62%.

In the normal tissue of oral mucosa squamous epithelia, the expression of FGFR3 protein is observed in the cytoplasm of prickle cells, whereas in the tissue of oral squamous cell carcinoma having no mutation the expression was observed in the cytoplasm and the nucleus. On the other hand, in cases that have a FGFR3 G2128T mutation, FGFR3 protein was strongly expressed on the cell membrane.

Johnston et. al[56)] reported that FGFR1, FGFR2 and FGFR4 were expressed in the cytoplasm of the COS cells and FGFR3 was expressed in the nucleus as measured by the immunofluorescent staining method using specific antibody, whereas when the cells were allowed to excessively express wild type FGFR3, the expression of FGFR3 was observed on the membrane. It is believed that in oral squamous cell carcinoma having a G2128T mutation of FGFR3, FGFR3 protein is excessively expressed on the cell membrane due to the mutation.

Although FGFR is synthesized in the cytoplasm, it is thought that receptor proteins observed in the cytoplasm have no activity and the receptor proteins expressed on the membrane are activated to function. Therefore, FGFR3 protein that is excessively expressed on the cell membrane observed in mutation cases is believed to be functioning. In the normal cells also, it is thought, FGFR expression on the membrane is not entirely absent, but no positive findings were observed due to its small amount expressed, but FGFR is significantly expressed on the membrane in mutation cases.

Thus, the difference in localization of protein expression is considered to indicate not only the difference in the amount expressed but, in the case of receptor proteins, the difference in their functions, Thus, the function of FGFR3 was investigated.

FGFR is considered to be a molecule that binds FGF and thereby is involved in signal transduction of cell growth, differentiation, and the like. Among others, FGFR3 is thought to control the growth and differentiation of normal cells as described below.

Su et al.[57] have conducted gene transfer to 293T calls of a mutant FGFR3 having Lys650Glu observed in TDII and demonstrated that the mutated FGFR3 exhibits a permanent tyrosine kinase activity. Deng et al.[58] have demonstrated the promotion of bone growth in FGFR3-deficient mice, and Colvin et al.[59] have constructed the FGFR3 knock-out mice and demonstrated that the mice exhibit a severe hearing loss derived from increased bone growth and differentiation hypoplasia of auris interna. Based on these results, they believe that FGFR3 signals work as signals involved in regulated growth in the bone.

On the other hand, Onose et al.[60] have analyzed the function of FGFR3 by excessively expressing FGFR3 in the thyroid cancer cells. They found that the cells in which FGFR3 was excessively expressed had no difference in growth rate compared to the control, whereas the cells excessively expressing FGFR3 continued to grow even after the control group stopped the cell growth, suggesting the possibility that FGFR3 is involved in the control of contact growth inhibition.

In order to investigate the functional significance of Gly697Cys mutation of FGFR3 in oral squamous cell carcinoma, the present inventor has conducted the expression of a wild type protein and a Gly697Cys mutated protein in the intracellular region of FGFR3 in the baculovirus expression system, and compared their tyrosine kinase phosphorylation activity, with a result that the mutant showed an increased activity of self-phosphorylation. The result suggests that the mutation causes a ligand-independent permanent self-phosphorylation of FGFR3 and promotes signaling of FGFR3, rendering normal cell differentiation uncontrollable and, at the same time, negating growth inhibition by cell-to-cell contact, which results in the canceration of oral squamous cells.

The findings related to the present invention may be summarized as follows:

In about 62% (44 out of 71 cases) of oral squamous cell carcinoma, the mutation (G2128T) of the base guanine at position 2128 of FGFR3 to thymine was observed. This mutation results in the substitution (Gly697Cys) of the amino acid glycine at position 697 of the FGFR3 protein with cysteine.

As a result of immunohistological examination of the expression of FGFR3 protein in normal oral mucosal squamous epithelia and oral squamous cell carcinoma, the expression of FGFR3 protein was found in the cytoplasm of prickle cells of the normal epithelia and the over-expression of FGFR3 protein on the cell membrane was noted in mutated case, whereas FGFR3 was localized in the cytoplasm and the nucleus in mutation-free cases.

The wild type and the mutant FGFR3 tyrosine kinase proteins were allowed to be expressed by recombinant gene technology using the baculovirus system in order to compare phosphorylation activity, and it was shown that the tyrosine kinase phosphorylation activity was enhanced in the mutant type compared to the wild type.

The result shown below demonstrates that in oral squamous cell carcinoma a Gly697Cys substitution based on the G2128T mutation occurs at a high frequency in the FGFR3 tyrosine kinase region, indicating that FGFR3 is useful as a molecular target for gene diagnosis and therapy.

It can also been seen that the Gly697Cys mutation, by causing permanent activation of FGF-independent FGFR3 tyrosine kinase, is deeply involved in the onset and progression of oral squamous cell carcinoma.

In accordance with the present invention, therefore, by investigating the presence of mutation of the base at position 2128 of the FGFR3 gene in oral squamous epithelial cells of interest, it can be judged whether the cells are oral squamous cell carcinoma or not, and thereby said mutation can be used as a useful molecular target marker for gene diagnosis and therapy of oral squamous cell carcinoma.

The present invention will now be explained in more detail with reference to examples of oral squamous cell carcinoma, but it should be noted that the present invention is not limited by these examples in any way.

EXAMPLE 1

Mutation of FGFR3 in Oral Squamous Cell Carcinoma (OSCC)

(1) Materials

Paraffin-embedded blocks of 71 cases that were histopathologically diagnosed as squamous cell carcinoma during four years and a year from January 1996 to June 2000 were used. The TNM classification and the stage classification were made based on the UICC (1987) classification[29] (Table 1.

A list of oral squamous cell carcinoma cases

| Case No. | Age | Sex | Subsite | TNM classification | STAGE classification |
|---|---|---|---|---|---|
| 1 | 64 | F | tongue | T2N1M0 | III |
| 2 | 64 | F | lower mandible | T4N0M0 | IV |
| 3 | 54 | F | tongue | T1N0M0 | I |
| 4 | 80 | F | lower gingiva | T4N0M0 | IV |
| 5 | 62 | M | maxilla | T2N0M0 | II |
| 6 | 74 | M | buccal mucosa | T2N0M0 | II |
| 7 | 66 | M | tongue | T4N0M0 | IV |
| 8 | 63 | M | maxilla | T4N0M0 | IV |
| 9 | 39 | F | tongue | T1N0M0 | I |
| 10 | 54 | M | tongue | T3N0M0 | III |
| 11 | 81 | F | tongue | T2N0M0 | II |
| 12 | 79 | M | maxilla | T4N0M0 | IV |
| 13 | 66 | F | upper gingiva | T2N0M0 | II |
| 14 | 68 | M | lower mandible | T4N0M0 | II |
| 15 | 67 | F | upper gingiva | T4N0M0 | IV |
| 16 | 68 | M | lower mandible | T3N2M0 | IV |
| 17 | 52 | M | tongue | T2N0M0 | II |
| 18 | 72 | F | lower mandible | T3N1M0 | III |
| 19 | 74 | F | lower mandible | T1N0M0 | I |
| 20 | 70 | F | buccal mucosa | T4N0M0 | IV |
| 21 | 61 | M | lower gingiva | T3N0M0 | III |
| 22 | 64 | M | soft palate | T1N0M0 | I |
| 23 | 71 | F | lower mandible | T4N0M0 | IV |
| 24 | 82 | M | maxilla | T4N0M0 | IV |
| 25 | 56 | M | tongue | T1N0M0 | I |
| 26 | 59 | M | maxilla | T4N0M0 | IV |
| 27 | 88 | F | tongue | T2N0M0 | II |
| 28 | 65 | F | tongue | T2N0M0 | II |
| 29 | 68 | F | lower mandible | T1N2M0 | IV |
| 30 | 78 | M | buccal mucosa | T1N0M0 | I |
| 31 | 75 | M | floor of mouth | T2N0M0 | II |
| 32 | 75 | M | maxilla | T4N0M0 | IV |
| 33 | 81 | F | buccal mucosa | T2N1M0 | III |
| 34 | 51 | M | tongue | T4N0M0 | IV |
| 35 | 68 | M | tongue + floor of mouth | T4N2cM0 | IV |
| 36 | 79 | F | lower mandible | T2N0M0 | II |
| 37 | 38 | M | tongue | T2N0M0 | II |
| 38 | 61 | M | maxilla | T3N0M0 | III |
| 39 | 49 | F | tongue | T3N0M0 | III |
| 40 | 71 | M | tongue + lower mandible | T1N0M0 | I |
| 41 | 69 | M | lower gingiva | T2N0M0 | II |
| 42 | 74 | M | floor of mouth | T4N2bM0 | IV |
| 43 | 57 | M | maxilla | T4N0M0 | IV |
| 44 | 89 | F | floor of mouth | T4N2bM0 | IV |
| 45 | 72 | M | lower mandible | T4N2bM0 | IV |

-continued

A list of oral squamous cell carcinoma cases

| Case No. | Age | Sex | Subsite | TNM classification | STAGE classification |
|---|---|---|---|---|---|
| 46 | 51 | F | tongue | T2N2bM0 | IV |
| 47 | 66 | M | lower mandible | T2N0M0 | II |
| 48 | 56 | M | tongue | T1N0M0 | I |
| 49 | 64 | F | upper gingiva | T4N0M0 | IV |
| 50 | 74 | M | lower mandible | T4N0M0 | IV |
| 51 | 88 | F | buccal mucosa | T1N0M0 | I |
| 52 | 67 | F | lower mandible | T2N2bM0 | IV |
| 53 | 65 | F | tongue | T1N0M0 | I |
| 54 | 75 | F | maxilla + lower mandible | T4N0M0 | IV |
| 55 | 67 | M | floor of mouth | T2N0M0 | II |
| 56 | 47 | M | lower mandible | T2N0M0 | II |
| 57 | 67 | F | lower mandible | T2N0M0 | II |
| 58 | 59 | F | tongue | T3N2bM0 | IV |
| 59 | 67 | F | tongue | T1N0M0 | I |
| 60 | 58 | M | tongue + floor of mouth | T4N2bM0 | IV |
| 61 | 56 | M | tongue | T1N0M0 | I |
| 62 | 69 | M | lower gingiva | T2N2bM0 | IV |
| 63 | 77 | F | floor of mouth | T2N0M0 | II |
| 64 | 68 | M | lower mandible | T4N0M0 | IV |
| 65 | 66 | F | upper gingiva | T2N0M0 | II |
| 66 | 68 | M | floor of mouth | T2N0M0 | II |
| 67 | 56 | M | upper gingiva | T4N0M0 | IV |
| 68 | 73 | M | lower mandible | T4N0M0 | IV |
| 69 | 56 | F | hard palate | T1N0M0 | I |
| 70 | 64 | F | tongue | T4N0M0 | IV |
| 71 | 73 | M | upper gingiva | T3N0M0 | III |

(2) Extraction of DNA

The extraction of DNA from the paraffin-embedded pathological specimens was performed using the DNA extraction kit DEXPAT (TakaRa). DNA after extraction was precipitated in 1/10 volume of 3M sodium acetate and 2.5 volumes of 100% ethanol, and after purification, it was determined using a spectrophotometer (manufactured by Beckman-Coulter).

(3) Polymerase Chain Reaction (PCR)

PCR[301] was performed according to the method of Kawasaki et al.[311]. Primer pairs that amplify each of exons 10 to 19 that correspond to the entire exons of the intracellular region of the FGFR3 gene were designed in the intron portions as follows[131]:

```
exon 10   Upstream 5'-CTA GAG TCA CTG GCG TTA C-3'
                   (SEQ ID NO. 4)
          Down-    5'-GCA GCT CAG AAC CTG GTA T-3'
          stream   (SEQ ID NO. 5)

exon 11   Upstream 5'-CCT GCT GAC CCA AGC AGG T-3'
                   (SEQ ID NO. 6)
          Down-    5'-CCT ACA GCC AAC GCT GGC C-3'
          stream   (SEQ ID NO. 7)

exon 12   Upstream 5'-CCT TAC GAA CAG TCT GTA GG-3'
                   (SEQ ID NO. 8)
          Down-    5'-CAT CGT CTG TGC ACG GAG C-3'
          stream   (SEQ ID NO. 9)

exon 13   Upstream 5'-CGC TCC GTG CAC AGA CGA TG-3'
                   (SEQ ID NO. 10)
          Down-    5'-CCT CAG ACG GGC TGC CAG G-3'
          stream   (SEQ ID NO. 11)

exon 14   Upstream 5'-GTA GGT GCG GTA GCG GCG-3'
                   (SEQ ID NO. 12)
          Down-    5'-CTC CCA GCA TCT CAG GGC-3'
          stream   (SEQ ID NO. 13)

exon 15   Upstream 5'-TGC CCT GAG ATG CTG GGA G-3'
                   (SEQ ID NO. 14)
          Down-    5'-GCT CAC GTT GGT TGT CTT C-3'
          stream   (SEQ ID NO. 15)

exon 16   Upstream 5'-CAT GCC AGT AGG ACG CCT G-3'
                   (SEQ ID NO. 16)
          Down-    5'-GCT GTC CTG AGA CTC CCA G-3'
          stream   (SEQ ID NO. 17)

exon 17   Upstream 5'-GAC CGA GTC TAC ACT CAC C-3'
                   (SEQ ID NO. 18)
          Down-    5'-GAC AGG TCC AGG TAC TCG T-3'
          stream   (SEQ ID NO. 19)

exon 18   Upstream 5'-GAC TCA CTC CTG AGC GCC C-3'
                   (SEQ ID NO. 20)
          Down-    5'-CGC ACA GCC ACC TCT GTG C-3'
          stream   (SEQ ID NO. 21)

exon 19   Upstream 5'-TCA CCC CGC CTC CCG CCA G-3'
                   (SEQ ID NO. 22)
          Down-    5'-CCA GTG GCC CTT CAC GTC CG-3'
          stream   (SEQ ID NO. 23)
```

PCR was performed using GENEAMP PCR Core kit (Perkin-Elmer Cetus Instrument Co. Ltd.), and DNA was amplified using the DNA thermal cycler (Perkin-Elmer Cetus Instrument Co. Ltd.). To the DNA extracted (0.02 μg), the PCR solution (10 mM Tris-HCl, pH 8.3, 50 mM KCl, 1.5 mM MgCl$_2$, 0.2 mM dNTP, 25 pM upstream primer, 25 pM downstream primer, 2.5 U AMPLITAQ DNA polymerase) was added to make the total volume of 25 μl, which was subjected to 35 cycles of a program with one cycle comprising a denaturation reaction at 95° C. for 30 seconds, an annealing reaction at 55° C. (exon 17), 58° C. (exon 10, 15), 60° C. (exon 11, 16), 64° C. (exon 18), 66° C. (exon 13), and 68° C. (exon 19) for 30 seconds each, and an elongation reaction at 72° C. for one minute to obtain PCR products. After the PCR products were electrophoresed on 1.2% agarose gel, they were visualized with etidium bromide.

(4) PCR-single Strand Conformation Polymorphism (PCR-SSCP)

The presence of mutation was investigated by PCR-SSCP for each exon. To 3.5 μl of the PCR product obtained in the above (3), an equal amount of the denaturation solution (95% formamide, 0.05% xylene cyanol, 0.04% bromophenol blue) was added, and treated at 95° C. for 5 minutes. After the denaturation of DNA, it was immediately cooled and made single stranded. Electrophoresis was conducted using the Gene Phor (Amersham Pharmacia Biotech) under the Condition of 600 V, 25 mA, and 15° C. As the SSCP gel, GeneGel Excel 12.5/24 Kit (Amersham Pharmacia Biotech) was used. After the electrophoresis, the gel was stained with the PlusOne DNA silver staining kit (Amersham Pharmacia Biotech) to detect DNA bands.

(5) Determination of Base Sequences (the Direct Sequencing Method)

For exons for which the presence of mutation was predicted by PCR-SSCP, the base sequence was determined by the direct sequencing method to identify the mutation sites. To 1.5 μl of the PCR products obtained in the above (3), 3 μl of the pre-mix (DNA Sequencing Kit; Perkin-Elmer Cetus Instrument Co. Ltd.) and 10 pM of the upstream primer were added to make the total volume of 20 μl, which was then subjected to 25 cycles of a program with one cycle comprising a denaturation reaction at 96° C. for 20 seconds, an annealing reaction at 50° C. for 15 seconds, and an elongation reaction at 60° C. for 4 minutes, and then cooled at 4° C. The samples after the reaction were purified with four volumes of 100% ethanol and then 70% ethanol. The pellet obtained was dissolved in 13 µl of Template Suppression Reagent (Perkin-Elmer Cetus Instrument Co. Ltd.) and denatured at 95° C. for 5 minutes. Then the base sequence was determined using the ABI PRISM 310 Genetic Analyzer (Pekin-Elmer Cetus Instrument Co. Ltd.) by the terminator labeled method (Dye Terminator method).

(6) Result

Figure 3:
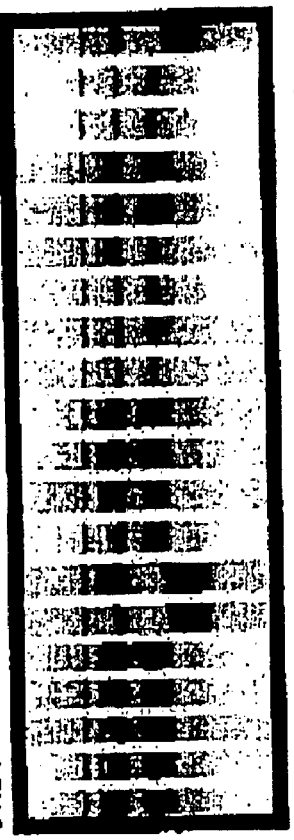
FIG. 3 shows the result of PCR-SSCP analysis of mutation in exon 17 of the FGFR3 gene.
Figure 3:
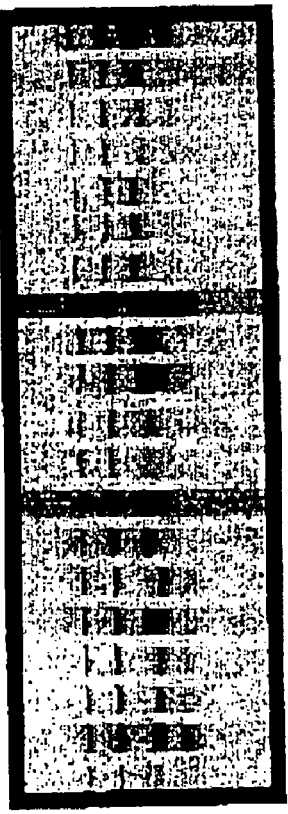
Figure 3:
Figure 3:
Figure 3:
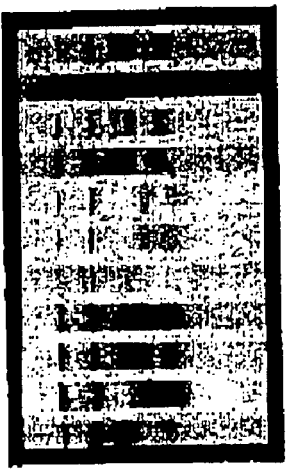
Figure 4:
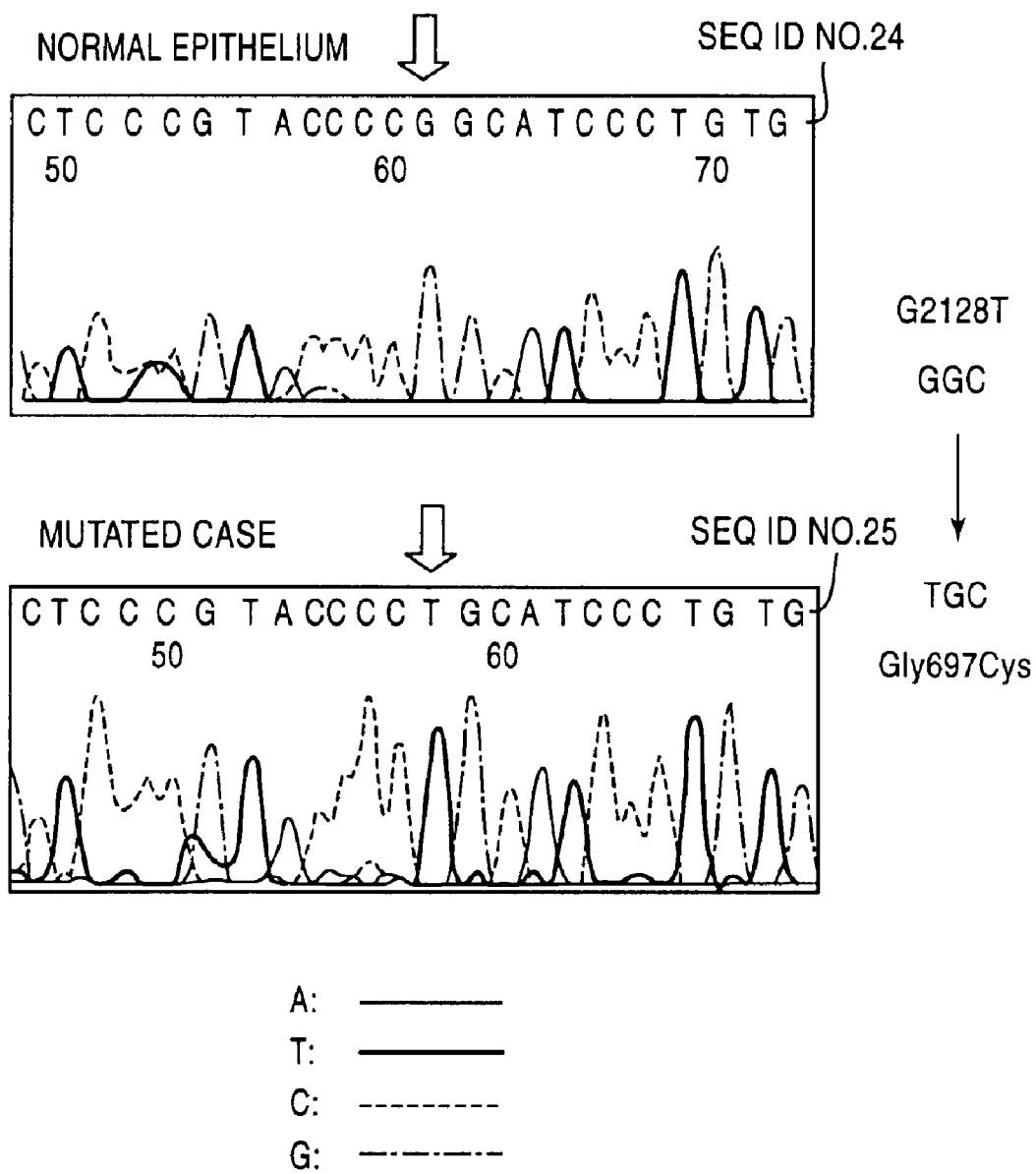
FIG. 4 shows the direction of the point mutation G2128T by the direst sequencing method. In the figures, a solid line (——) indicates the detection of A, a thick solid line (▬▬) indicates the detection of T, a broken line (------) indicates the detection of C, and an alternate long and short dash line (—·—) indicates the detection of G.

By investigating the presence of mutation from exon 10 to exon 19 of the FGFR3 intracellular region in the OSCC-derived DNA by PCR-SSCP, the presence of mutation was suggested in exon 17 of the FGFR3 gene (FIG. 3). No results were obtained that suggest the presence of mutation in the other exons. Thus, the base sequence on exon 17 was investigated using the direct sequencing method, and the point mutation (G2128T) in that the base guanine at position 2128 of FGFR3 was mutated to thymine was observed in all cases for that mutation was suggested by PCR-SSCP (FIG. 4). This was found in about 62%, or 44 out of 71 Cases. This mutation indicated the substitution (Gly697Cys) of the amino acid glycine at position 697 of the FGFR3 gene with cysteine.

EXAMPLE 2

Expression of FGFR3 Protein in the Tissues of Oral Squamous Cell Carcinoma and the Normal Epithelium (1) The expression of FGFR3 protein was investigated using the Vectastatin ABC kit (Vector Laboratories, Inc.) by the immunoperoxidase staining method based on avidin-biotin-peroxidase complex method (ABC method).

Sections of 4 µm in thickness were prepared on poly-L-lysine coated slides. After incubating at 37° C. for 4 days, they were hydrated with the xylene and ethanol series, and the endogenous peroxidase was removed by MeOH/0.3% H$_2$O$_2$ at room temperature for 30 minutes followed by treatment with 0.1% Triton X-100/PBS on ice for 10 minutes, and then 0.05% Protenass-K/PBS at room temperature for 5 minutes. In order to prevent nonspecific reactions, blocking was performed by 10% goat serum/PBS at 37° C. for 1 hour. Anti-FGFR3 rabbit polyclonal antibody (Santa Cruz Biotechnology, Inc.) as the primary antibody was allowed to react overnight at 4° C. Then biotin-labeled goat anti-rabbit IgG+IgA+IgM was allowed to react at 37° C. for 1 hour, and the avidin-biotin-peroxidase complex was reacted at room temperature for 30 minutes, and finally color was developed using the DAB solution (0.25 mg/ml 3,3-diaminobendizine, 0.01% H$_2$O$_2$, 50 mM Trio-HCL buffer, pH 7.6). The nucleus was stained with hematoxylin. As the control, anti-rabbit IgG was used.

(2) Result

Figure 5:
FIG. 5 shows the expression of FGFR3 protein in the cytoplasm.
Figure 6:
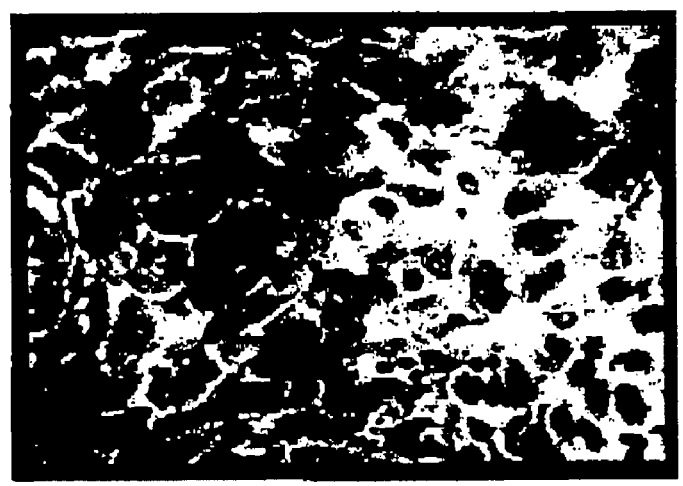
FIG. 6 shows the expression of FGFR3 protein in the tissue of oral squamous cell carcinoma having no G2128T mutation. The protein expression is seen in the cytoplasm and the nucleus.
Figure 7:
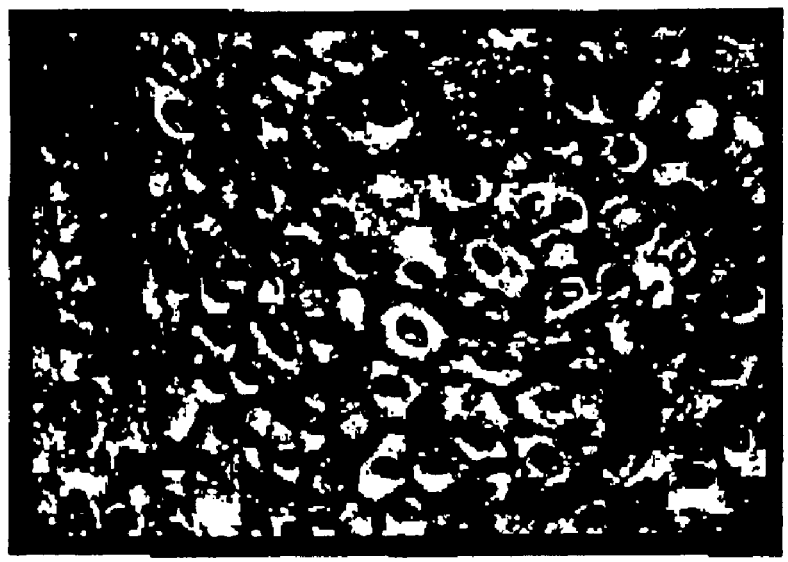
FIG. 7 shows the expression of FGFR3 protein in the tissue of oral squamous cell carcinoma having a G2128T mutation. The strong expression of the protein is seen in the cell membrane.

In the normal epithelial tissue, the expression of FGFR3 protein was observed in the cytoplasm of the prickle cells (FIG. 5). In the tissue of oral squamous cell carcinoma having no mutation in FGFR3, the expression of FGFR3 protein was observed in the cytoplasm and the nucleus of the cancer cells (FIG. 6). On the other hand, in the tissue of oral squamous cell carcinoma having the G2128T mutation, the strong expression of FGFR3 protein was observed in the cell membrane of the cancer cells (FIG. 7).

EXAMPLE 3

Study on the Tyrosine Kinase Phosphorylation Activity of the Wild Type and the G2128T Mutant FGFR3

(1) Extraction of RNA derived from the epithelial cells of normal human oral mucosa RNA extraction from cultured epithelial cells of normal human oral mucosa was performed according to the method of Chomozynski At al.[32]. After the cultured normal epithelial cells were harvested from the denaturation solution (4 M guanidinothiocyanate, 25 mM sodium citrate, pH 7.0, 0.1 M 2-mercaptoethanol, 0.5% N-laurylsarcocine), they were homogenized with a 20G injection needle. After adding 1/10 volume of 2 M sodium acetate, pH 4.0, total RNA was isolated using phenol/chloroform in which an equilibrated acidic phenol (phenol/TE) and phenol and chloroform were mixed in equal amounts. Then, one volume of isopropanol was added to precipitate RNA. The RNA was dissolved again in the denaturation solution to which one volume of isopropanol was added to precipitate RNA and to obtain total RNA.

(2) Construction of a wild type-FGFR3 tyrosine kinase expression vector

Specific primers that amplify from the ATP-biding site to the C-terminal of the tyrosine kinase region of FGFR3 were designed as follows:

```
Upstream    5'-TGG AAT TCA ACG CGT CCA TGA GCT CCA AC-3'  (SEQ ID NO:1)
Downstream  5'-CAG AAT TCC TTC ACG TCC GCG AGC CCC-3'    (SEQ ID NO:2)
```

Then using normal human epithelium-derived RNA, RT-PCR was performed. RT-PCR used GENEAMP RNA PCR Core kit (Perkin-Elmer Cetus Instrument Co. Ltd.), and DNA was amplified using the DNA thermal cycler (Perkin-Elmer Cetus Instrument Co. Ltd.). First, to the RT solution (10 mM Tris-HCl pH 8.3, 50 mM KCl, 5 mM MgCl$_2$, 1 mM dNTP, 1 U ribonuclease inhibitor, 2.5 mM random hexamer, 2.5 U MuLV reverse transcriptase), total RNA (1 µg/2 µl) was added, and a reverse transcription reaction was performed at 42° C. for 30 minutes and 99° C. for 5 minutes. Then the PCR solution (10 mM Tris-HCl, pH 8.3, 50 mM KCl, 1.5 mM MgCl$_2$, 0.2 mM dNTP, 25 pM upstream primer, 25 pM downstream primer, 2.5 U AMPLITAQ DNA polymerase) was added to make the total volume of 100 µl, which was subjected to 40 cycles with one cycle comprising a denaturation reaction at 95° C. for 45 seconds, an annealing reaction at 56° C. for 15 seconds, and an elongation reaction at 70° C. for two minutes and 45 seconds. After the PCR product obtained were purified with ethanol, it was treated with an the EcoRI restriction enzyme. On the other hand, pALTER-MAX vector (Promega) was treated with an EcoRI restriction enzyme and, to prevent self-ligation, treated with calf intestine-derived alkaline phosphatase (CIAP). To the vector an EcoRI-treated DNA was integrated to construct a wild type FGFR3 tyrosine kinase expression vector (FIG. 1). The base sequence of the vector was confirmed by the direct sequencing method.

(3) Construction of mutant FGFR3 tyrosine kinase expression vector

For the construction of a mutant FGFR3 tyrosine kinase expression vector having the G2128T mutation, the Altered Sites II mammal mutagenesis system (Promega Madison) was used.

First, an FGFR3 mutagenic oligonucleotide containing the G2128T mutation was designed as shown below:

5'-CCG TAC CCC TGC ATC CCT G-3'    (SEQ ID NO: 3)

Using this oligonucleotide and the vector constructed above (2), a mutant vector was constructed with the ES1301 MutS competent cells (Promega Madison), The vector was amplified with the JM109 competent cells (Promega Madison). The base sequence was confirmed by the direct sequencing method.

(4) Recombination of vectors

Figure 2:
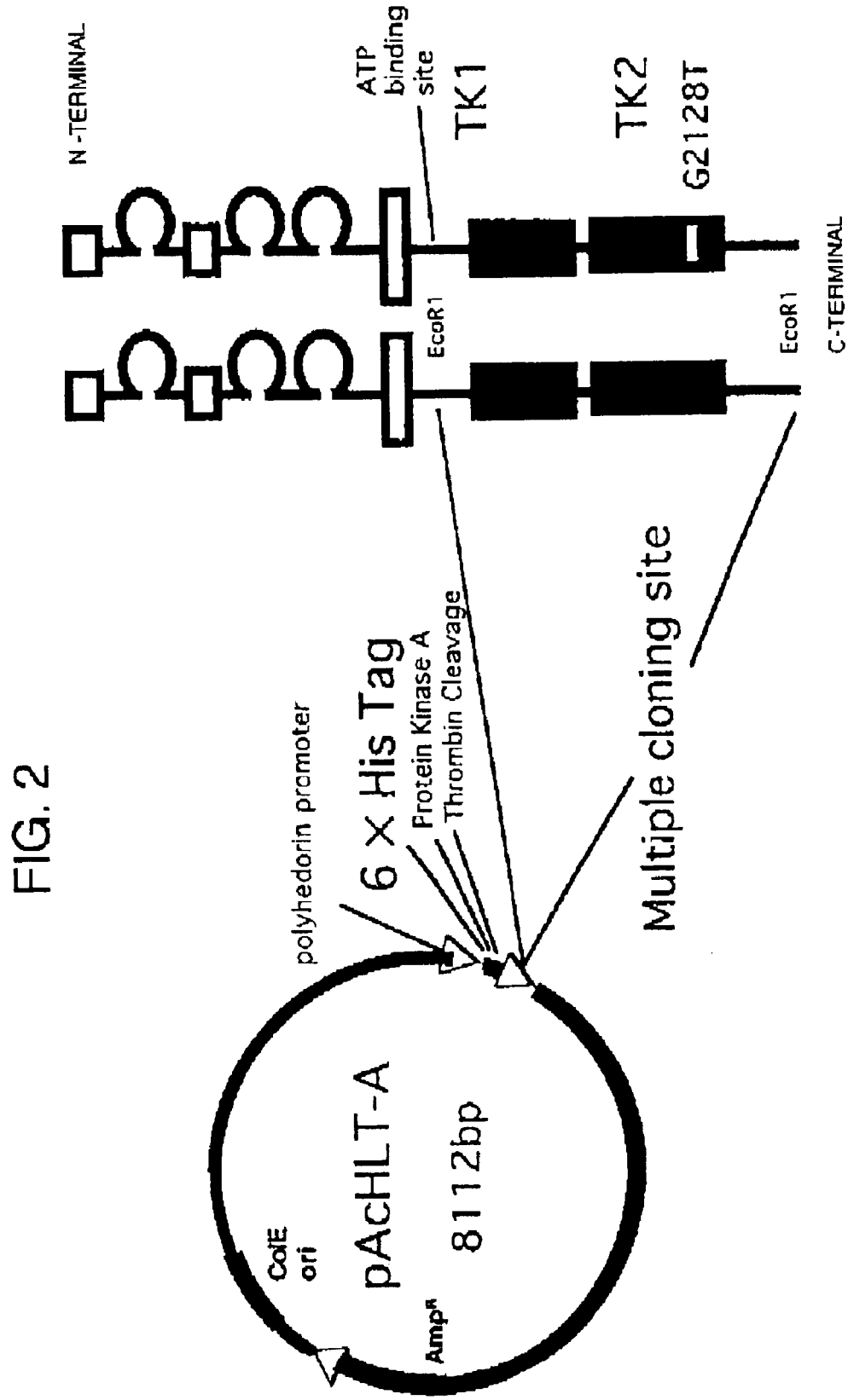
FIG. 2 shows the construction of a baculovirus expression vector.

The wild type and the mutant FGFR3 tyrosine kinase expression vector integrated into the pALTER-MAX vector constructed in the above (2) and (3) were recombined into the pAcHLT-A vector (Pharmingen) to which a histidine tag was added to the N-terminal (baculovirus expression vector) (FIG. 2).

(5) Culturing of insect cells

As the insect cell, Sf9 cells (Pharmingen) were used. The medium used was the Grace's Insect Medium Supplemented (GIBCO BRL) with 5% calf serum (Hy Clone), and sub-cultured in a 25 cm² flask (Falcon Cat. #3081). Culturing was performed in an incubator MIR-153 (SANYO) at 27° C.

(6) Co-transfection

Gene transfection was performed based on the baculovirus expression vector system (Pharmingen). First, the insect cell SF9 was plated to a 6 cm culture dish at a concentration of 2×10⁶, cells. On the other hand, 5 μg of BACULOGOLD DNA (Pharmingen) and 5 μg of DNA into which had integrated the wilt type and the mutant FGFR3 tyrosine kinase region constructed in the above (2) and (3) were mixed, allowed to stand for 5 minutes, to which was added 1 ml of the transfection buffer B (HEPES buffer). The medium was replaced with 1 ml of the transfection buffer A (10% CS Grace's medium), to which was slowly added the mixed solution, to perform co-transfection. After 4 hours, it was replaced with 5% CS-added Grace's insect medium. It was observed every day, and on day 5 when an infection image was observed it was subcultures.

(7) Preparation of samples

By repeating subculturing, virus titer was raised, and the culture supernatants of the wild type and the mutant were harvested. They was mixed with the Ni-NTA agarose (QIAGEN), and incubated at 4° C. for 1 hour. Then agarose was recovered by centrifugation, and then the phosphorylation reaction buffer (50 mM Tris-HCl, pH 6.8, 200 mM KCl, 0.1 mM ATP, 1 mM MgCl₂, 2 mM DTT, 1 mM PMSF) was added, and further reacted at 37° C. for 15 minutes. Immediately after the completion of the reaction, they were dissolved in a 4×SDS-PAGE loading buffer (200 mM Trig-HCl, pH 6.8, 400 mM DTT, 8% SDS, 40% glycerol, 0.04% bromophenol blue), and were treated at 100° C. for 10 minutes[331], (8) SDS-PAGE and Western blotting For each sample, protein was isolated using the SDS-polyacrylamide gel electrophoresis (SDS-PAGE) in the presence of 5% 2-mercaptoethanol. For separation 10% gel concentration and for concentration 4% gel concentration were used, respectively at a thickness of 1 mm. According to the method of Lastick et al.[341], electrophoresis was performed using the thermostat double minislab gel electrophoresis instrument (Nippon Eido) at 100 V for 2.5 hours. Using the Trans-Blot SD Semi-Dry Transfer Cell (Bio-Rad Laboratories), the gel was transferred to a PVDF membrane (Millipore) by applying 20 V for 2 hours. In order to inhibit nonspecific reactions, the PVDF membrane after the transfer was allowed to react with 5% defatted milk/TBS (50 mM Tris-HCl, pH 7.6, 150 mM NaCl)+0.1% Tween 20 at room temperature for 1 hour.

Thereafter, a 1000fold diluted anti-phosphotyrosine antibody (monoclonal antibody 4G10) (Upstate biotechnology Lake Placid) as the primary antibody was reacted at 4° C. overnight, and, as the second antibody, 1000-fold diluted goat anti-mouse IgG (E+L)-AP conjugate (Bio-Rad Laboratories) was reacted at room temperature for 1.5 hour. Color was developed using the BCIP/NBT Membrane Phosphatase Substrate System (Kirkgard & Perry Laboratories).

(9) Result

Figure 8:
FIG. 8 shows the result of Western blotting that demonstrates the difference in tyrosine phosphorylation of the wild type and the mutant proteins.

The intracellular, regions of the wild type and the G2128T mutated FGFR3 protein were constructed by the baculovirus expression system, and the tyrosine phosphorylation activity was compared using anti-phosphotyrosine antibody in the Western blotting method. As a result, few bands that exhibit tyrosine phosphorylation were confirmed in the wild type protein, whereas bands that exhibit apparently high tyrosine phosphorylation were detected in the mutant protein (FIG. 8), indicating that an enhanced tyrosine kinase phosphorylation activity was noted in the FGFR3 protein having a Gly697Cys amino acid substitution due to the G2128T mutation as compared to the Wild type.

EXAMPLE 4

Disappearance of G2128T Mutation by Chemotherapy and Radiation Therapy and Reversion to the Wild Type For patients with primary squamous cell carcinoma in the maxillary sinus, the FGFR3 gene derived from the cancer tissue before treatment was examined and the G2128T mutation was observed in exon 17.

This patient was treated with the "selective artery injection therapy" in which an indwelling catheter was inserted into the maxillary artery, a dominant artery of tumor. Via the catheter, lymphokine-activated killer cells (LAK cells), interleukin 2, and 5-FU (anticancer agent) were given in combination with radiation therapy. For the LAK cells, the patient peripheral blood-derived lymphocytes were cultured in a serum-free medium (RD5F) containing interleukin 2 for 1–2 weeks to induce LAK cells, and then a total of 8×10⁵ cells were given again to the patient via the catheter. Prior to the administration of the LAK cells, 1.2 million units of interleukin 2 (celeuk) was also given simultaneously via the catheter. A total of 2375 mg of 5-FU comprising 25 mg×14 days and 62.5 mg×10 days was given to the patient via the catheter. The radiation therapy was 2 Gy/day×26 days with a total of 55 Gy.

Figure 9:
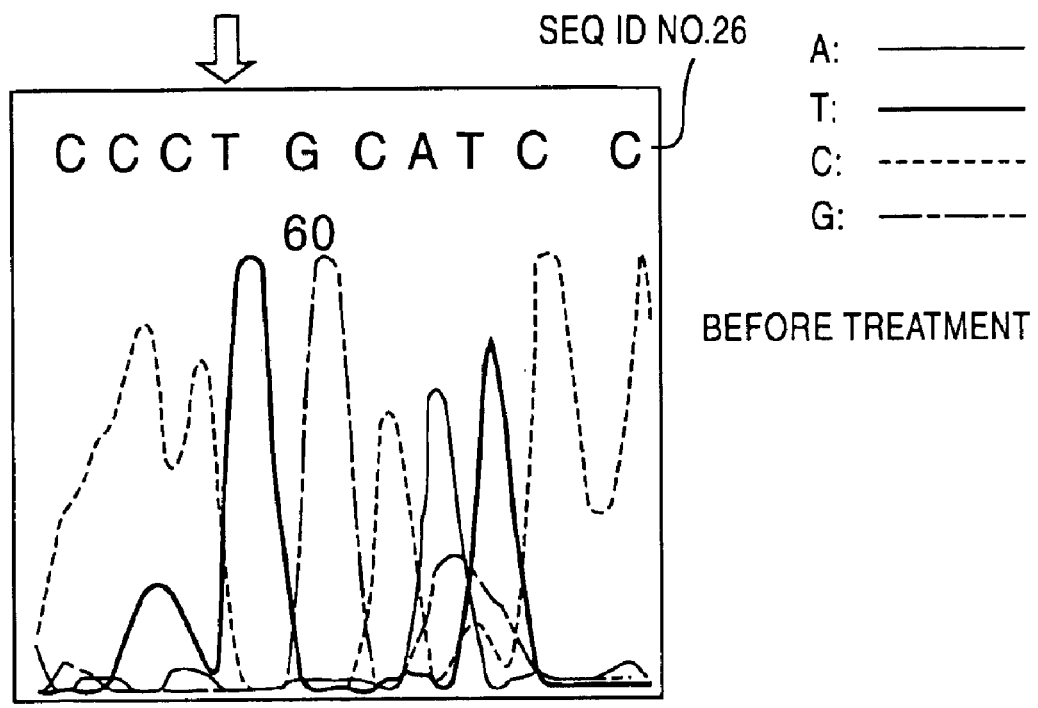
FIG. 9 shows the result of the direct sequencing method indicating the disappearance of a G2128T mutation and reversion to the wild type after chemotherapy and radiation therapy in primary squamous sell carcinoma in the maxillary sinus. In the figures, a solid line (——) indicates the detection of A, a thick solid line (▬▬) indicates the detection of T, a broken line (------) indicates the detection of C, and an alternate long and short dash line (—·—) indicted the detection of G.
Figure 9:
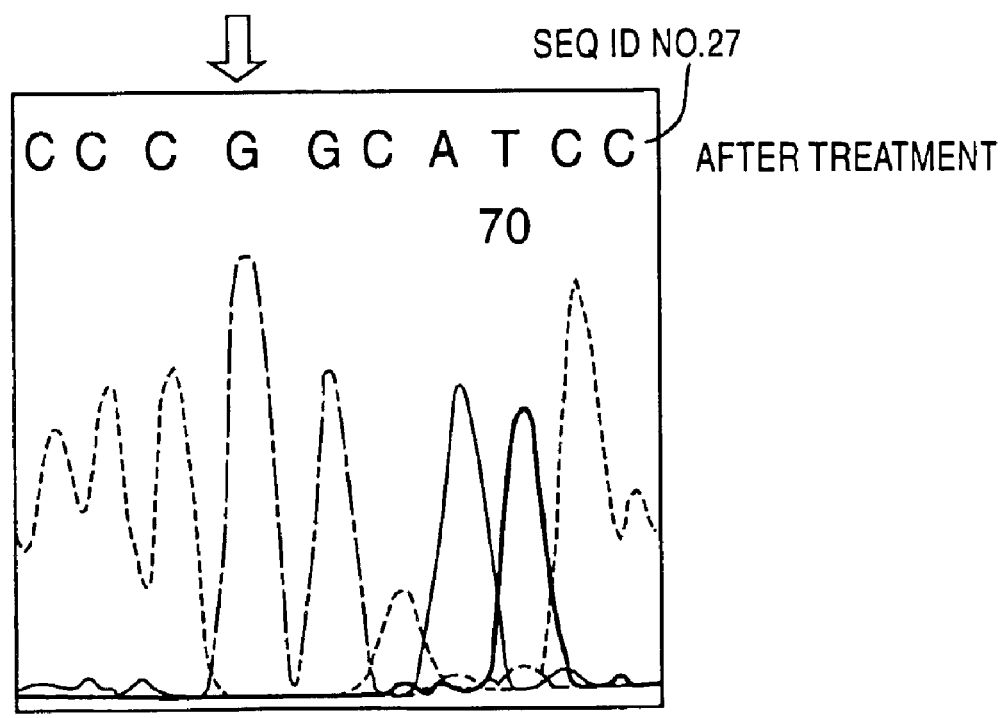

In DNA derived from tumor tissue from the same patient after the treatment with LAK cells, interleukin 2, 5-FU, and radiation therapy, the G2128T mutation disappeared and reverted to the wild type FGFR3. The result is shown in FIG. 9

REFERENCES

1) Gospodarowics, D., Jones, K. L., Sato, G.: Purification of a growth factor for ovarian cells from bovine pituitary glands Proc-Natl-Acad-Sci-USA., 71:2295–2299, 1974

2) Nishimura, T., Nakatake, Y., Konishi, M., Itoh, N.: Identification of novel FGF, FGF-21, preferentially expressed in the liver[1]. Biochem Biophys-Acta; 1492:203–206, 2000

3) Johnson, D. E., Williams, L. T.: Structural and functional diversity in the FGF receptor multigene family. Advances in Cancer-Res.; 60:1–41, 1993

4) Adnane, J., Gausray, F., Dionne, C. A., Crumley, G., Jaye, M., Schlessinger, J., Jeanteur, P., Birnbaum, D., Theillet, C.: BEK and FLG, two receptors to member of the FGF family, are amplified in subsets of human breast cancers. Oncogene; 6:659–663, 1991

5) Muenke, M., Shell, U.: Fibroblast growth factor receptor mutations in human skeletal disorders. Trends in Genetics; 11:308–313, 1995

6) Mason, I. J.: The ins and outs of fibroblast growth factors. Cell; 78: 547–552, 1994

7) Heldin, C. H.: Dimerization of cell surface receptors in signal transduction. Cell; 80:213–223, 1995

8) Ornitz, D. M.: FGFs, heparan sulfate and FGFRs: complex interactions essential for development. Bio Essays; 22:108–112, 2000

9) Isacchi, A., Bergonzoni, L., Sarmientos, P.; Complete sequence of human receptor for acidic and basic fibroblast growth factors, Nucl-Acid-Res.; 18:1906, 1990

10) Johnson, D. M. Lee, P. L., Lu, J., Williams, L. T.: Diverse forms of a receptor for acidia and basic fibroblast growth factors. Mole-Cell-Biol.; 10:4728–4736, 1990

11) Dionne, C. A., Crumley, G., Bellot, F., Kaplow, J. M., Searfoss, G., Ruta, M., Burgess, W. H., Jaye, M., Schlessinger, J.; Cloning and expression of two distinct high-affinity receptor cross-reacting with acidic and basic fibroblast growth factors, EMBO-J.; 9;2685–2692, 1990

12) Houssaint, E., Blanquet, P. R., Champion, Arnaud, P., Gesnel, M. C., Torriglia, A., Courtois, Y., Breathnach, R.: Related fibroblast growth factor receptor genes exist in the human genome. Proc-Natl-Acad-Sci-USA.; 87:8180–8184, 1990

13) Keegan, K., Johnson, D. E., Williams, L. T., Hayman, M. J.: Isolation of an additional member of the fibroblast growth factor receptor family, FGFR-3. Proc-Natl-Acad-Sci-USA.; 88:1095–1099, 1991

14) Thompson, L. M., Plummer, S., Schalling, M., Altherr, M. R., Gusella, J. F., Housman, D. E., Wasmuth, J. J.: A gene encoding a fibroblast growth factor receptor isolated from the Huntington disease gene region of human chromosome 4, Genomics; 11:1133–1142, 1991

15) Partanen, J., Makela, T. P., Eerola, E., Korhonen, J., Hirvonen, H., Claesson, Welsh, L., Alitalo, K,; FGFR-4, a novel acidic fibroblast growth factor receptor with a distinct expression pattern. EMBO-J.; 10:1347–1354, 1991

16) Vainkka, S., Partanen, J., Bellosta, P., Coulier, F., Birnbaum, D., Basilica, C., Jaye, M., Alitalo, K.: Fibroblast growth factor receptor-4 shows novel features in genomic structure, ligand binding and signal transduction. EMBO-J; 11:4273–4280, 1992

17) Jaye, M., Schlessinger, J., Dionne, C. A.: Fibroblast growth factor receptor tyrosine kinases: molecular analysis and signal transduction. Biochem-Biophys-Acta.; 1135:185–199, 1992

18) Ornits, D. M., Xu, J., Colvin, J. S., McEwen, D. G., MacArthur, C. A., Coulier, F., Gao, G., Goldfarb, M.: Receptor specificity of the fibroblast growth factor family. J-Biol-Chem; 271:15292–15297, 1996

19) Avivi, A., Yayon, A., Givol, D.: A novel form of FGF receptor-3 rising an alternative exon in the immunoglobulin domain III. FEBS-lett.; 330:249–252, 1993

20) Murgue, B., Tsunekawa, S., Rosenberg, I,, deBeaumont, M., Podolsky, D. K.: Identification of a novel variant form of fibroblast growth factor receptor 3(FGFR3III b) in human colonic epithelium. Cancer-Res.; 54:5206–5211, 1994

21) Johnson, D. E., Lu, J., Chen, H., Werner, S., Williams, L. T.; The human fibroblast growth factor receptor genes: a common structural arrangement underlies the mechanisms for generating receptor forms that differ in their third immunoglobulin domain. Mol-Cell-Biol, 11:4627–4634, 1991

22) Werner, S., Duan, D. S., de Vries, C., Peters, K. G., Johnson, D. E., Williams, L. T.: Differential splicing in the extracellular region of fibroblast growth factor receptor 1 generates receptor variants with different ligand-binding specificities. Mol-Cell-Biol; 12:82–88, 1992

23) Shi, E., Kan, M., Xu, J. Wang, F. Hou, J., McKeehan, W. L.: Control of fibroblast growth factor receptor kinase signal transduction by heterodimerization of combinatorial splice variants, Mol-Cell-Biol; 13:3907–3918, 1993

24) Chellaiah, A. T., McEwen, D. G., Werner, S., Xu, J., Orinitz, D. M.: Fibroblast growth factor receptor (FGFR) 3. J-Biol-Chem; 269:11620–11627, 1994

25) Webster, M. X., Donoghue, D. J.: FGFR activation in skeletal disorders: too much of a good thing. Trends in Genetics; 13:178–182, 1997

26) Gorlin, R. J: Fibroblast growth factors, their receptors and receptor disorders. J-Cranio-Maxillofacial-Surgery; 25:69–79, 1997

27) Drugan, C. S., Paterson, I. C., Prime, S. S.: Fibroblast growth factor receptor expression reflects cellular differentiation in human oral squamous carcinoma cell lines. Carcinogenesis; 19:1153–1156, 1998

28) Myoken, Y. Myoken, Y., Okamoto, T., Sato, J. D., Takada, K.: Immunocytochemical localization of fibroblast growth factor-1 (FGF-1) and FGF-2 in oral squamous cell carcinoma (SCC). J-Oral-Pathol-Med.; 23:451–456, 1994

29) TNM classification of malignant tumors, $4^{th}$ ED. UICC-International-Union-Against-Cancer; Springer-Verlag, 1987

30) Saiki, R. K., Gelfand, D. H., Stoffel, S., Scharf, S. J., Higuchi, R., Horn, G. T., Mullis, K. B., Erlich, H. A.: Primer-directed enzymatic amplification of DNA with a thermostable DNA polymerase. SCIENCE; 239:467–491, 1988

31) Kawasaki, E. S., Clark, S. S., Coyne, M. Y., Smith, S. D., Champlin, R.,Witte, O. N., McCormick, F. P.: Diagnosis of chronic myeloid and acute lymphocytic leukemias by detection of leukemia-specific mRNA sequences amplified in vitro. Proc-Natl-Acad-Sci-USA; 85:5698–5702, 1988

32) Chomczynski, P., Sacchi, N. Single-step method of RNA isolation by acid guanidinium thiocyanate-phenol-chloroform extraction. Anal-Biochem.; 162:156–159, 1937

33) Kasahara, M., Ohmori, M.: Activation of a cyanobacterial adenylate cyclase, CyaC, by autophosphorylation and a subsequent phosphotransfer reaction. J-Biol-Chem; 274:15167–15172, 1999

34) Lastick, S. M., McConkey, E. D.: Exchange and stability of HeLa ribosomal proteins in vivo. J-Biol-Chem; 251:2867–2875, 1976

35) Towbin, H., Staehelin, T., Gordon, J.: Electrophoretic transfer of proteins from polyacrylamide gels to nitrocellulose sheets: procedure and some applications. Proc-Natl-Acad-Sci-USA; 76:4350–4354, 1979

36) Reardon, W., Winter, R. M., Rutland, P., Pulleyn, L. J., Jones, B. M., Malcom, S.: Mutations in the fibroblast growth factor receptor 2 gene cause Crouzon syndrome. Nat-Genet.; 8:98–103, 1994

37) Jabs, E. W., Li, X., Scott, A. F., Meyers, G., Chen, W., Eccles, M., Mao, J., Charnas, L. R., Jackson, C. E., Jaye, M.; Jackson-Weiss and Crouzon syndromes are allelic with mutations in fibroblast growth factor receptor 2. Nat-Genet.; 8:275–279, 1994
38) Li, X., Park, W. J., Pyeritz, I. E., Jabs, E. W.: Effect on splicing of a silent FGFR2 mutation in Crouzon syndrome. Nat-Genet.; 9:232–233,1995
39) Muenke, M., Schell, U., Hehr, A., Robin, N. H., Loskenm, H. W., Schinzel, A., Pulleyn, L. J., Rutland, P., Reardon, W., Malcolm, S.,Winter,R. M., A common mutation in the fibroblast growth factor receptor 1 gene in Pfeiffer syndrome. Nat-Genet.; 8:269–274, 1994
40) Rutland, P., Pulleyn, L. J., Reardon, W., Baraitser, M., Hayward, R.,Jones, B., Malcom, S., Winter, R. M., Oldridge, M., Slaney, S. F., Poole, M. D., Wilkie, A. O. M.: Identical mutations in the FGFR2 gene cause both Pfeiffer and Crouzon syndrome phenotypes. Nat-Genet; 9:173–176, 1995
41) Lajeunie, E., Ma, H. W., Bonaventure, J., Munnich, A., Merrer, M. L. FGFR2 mutations in Pfeiffer syndrome. Nat-Genet.; 9:108, 1995
42) Shell, U., Hehr, A., Feldman, G. J., Robin, N. H. Zackai, E. H., Die Smulders, C., Viskochil, D. H., Stewart, J. M., Wolff, G., Ohashi, H., Price, R. A., Cohen, Jr., M. M., Muenke, M.: Mutations in FGFR1 and FGFR2 cause familial and sporadic Pfeiffer syndrome. Hum-Mole-Genet.; 4:323–328, 1995
43) Wilkie, A. O. M., Slaney, S. F., Oldridge, M., Poole, M. D., Ashworth, G. J., Hockley, A. D., Hayward, R. D., David, D. J., Pulleyn, L. J., Rutland, P., Malcolm, S., Winter, R. M., Reardon, W.; Apert syndrome results from localized mutations of FGFR2 and is allelic with Crouzon syndrome. Nat-Genet.; 9:165–171, 1995
44) Shiang, R., Thompson, L. M, Zhu, Y. Z., Church, D. M., Fielder, T. J., Bocian, M., Winokur, S. T., Bocian, M,, Winokur, S. T,, Wasmuth, J. J.:Mutations in the transmembrane domain of FGFR3 cause the most common genetic form of dwarfism, achondroplasia. Cell; 78:335–342, 1994
45) Rousseau, F., Bonaventure, J., Legeal M. L., Pelet, A., Rozrt, J. M.,Maroteaux, P., Merrer, M. L., Munnich, A.: Mutations in the gene encoding fibroblast growth factor receptor-3 in achondroplasia. NATURE; 371:252–254, 1994
46) Tavormina, P. L., Shiang, R., Thompson, L. M., Zhu, Y. Z., Wilkin, D. J., Lachman, R. S. Wilcox, W. R., Rimoin, D. L., Cohn, D. H., Wasmuth, J. J.; thanatophoric dysplasia (types I and II) caused by distinct mutations in fibroblast growth factor receptor 3. Nat-Genet.; 9:321–328, 1995
47) Meyers, G. A., Orlow, S. J., Munro, I. R., Przylepa, K. A., Jabs, E. W.; Fibroblast growth factor receptor 3(FGFR3) transmembrane mutation in Crouzon syndrome with acanthosis nigricans. Nat-Genet.; 11:462–464,1995
48) Sakata, K,. Alterations of tumor suppressor genes and the H-ras oncogenes in oral squamous cell carcinoma. J-Oral-Pathol-Med.;25:302–307,1996
49) Ramchurren, N., Cooper, K., Summerhayes, I. C. Molecular events underlying schistosomiasis-related bladder cancer. Int-J-Cancer; 62:237–244, 1995
50) Sakai, F,, Rikimaru, K., Ueda, M., Matsumoto, Y, Ishii, N., Enomoto, S., Yamamoto, H., Tsuchida, N.: The p53 tumor-suppressor gene and ras oncogene mutations in oral squamous-cell carcinoma. Int-J-Cancer; 52:867–872, 1992
51) Shibata, M. A., Shirai, T., Ogawa, K., Takahashi, S., Wild, C. P., Montesano, R., Tsuda, H., Ito, N.: DNA methylation adduct formation and H-ras gene mutations in progression of N-butyl-N-(4-hydroxybutyl) nitrosamine-induced bladder tumors caused by a single exposure to N-methyl-N-nitrosourea. Carcinogenesis; 15:2965–2968, 1994
52) Dawson, C. D., Chang, K. W., Solt, D. B. MTS1 gene mutations in archival oral squamous cell carcinoma. J-oral-Pathol-Med.; 25:541–546, 1996
53) Lang, J. C., Tobin, E. J., Konbloch T. J., Schuller, D. E., Bartynski, K. J., Mountain, R. E., Micholson, R., De Yonug, B. R., Weghorst, C. M.:Frequent mutation of p16 in squamous cell carcinoma of the head and neck. Laryngoscope; 108:923–928, 1998
54) Gunduz, M., Ouchida, M. , Fukushima, K., Hanafusa, H., Etani, T., Nishioka, S., Nishizaki, K., Shimizu, K.. Genomic structure of the humanING1 gene and tumor-specific mutations detected in head and neck squamous cell carcinomas. Cancer-Res.; 60:3143–3146, 2000
55) Oki, E., Maehara, Y., Tokunaga, E., Kakeji, Y., Sugimachi, K.: Reduced expression of p33(ING1) and the relationship with p53 expression in human gastric cancer. Cancer-Lett,; 147:157–162, 1999
56) Johnston, C. L., Cox, H. C., Gomm, J. J., Coombes, R. C. Fibroblast growth factor receptors (FGFR) localize in different cellular compartment. J-Biol-Chem; 270:30643–30650, 1995
57) Su, W. S. Kitagawa, M., Xue, N., Xie, B., Garofalo, S., Cho, J., Deng, C., Horton, W. A.,Fu, X. Y.: Activation of STAT1 by mutant fibroblast growth-factor receptor in thanatophoric dysplasia type II dwarfism. NATURE; 386;238–292, 1997
58) Deng, C., Wynshaw Doris, A., Zhou, F., Kuo, A., Leder, P.: Fibroblast growth factor receptor 3 is a negative regulator of bone growth, Cell; 84:911–921, 1996
59) Colvin, J. S,, Bohne, B. A., Harding, G. W., McEwen, D. G., Ornitz, D. M.:Skeletal overgrowth and deafness in mice lacking fibroblast growth factor receptor 3. Nat-Genet.; 12:390–397, 1996
60) Onose, H., Emoto, N., Sugihara, H., Shimizu, K., Wakabayashi, I.: Overexpression of fibroblast growth factor receptor 3 in a human thyroid carcinoma cell line results in overgrowth of the confluent cultures. European-J-Endocrinology; 140:169–173, 1999

What is claimed is:

1. A method of testing squamous epithelial cells to determine if said cells can progress into squamous cell carcinoma comprising testing squamous epithelial cells isolated from a human for the presence of the G2128T mutation in the FGFR3 gene, and determining that said cells can progress into squamous cell carcinoma if said mutation is present.

2. method of claim 1, wherein said squamous epithelial cells are from the maxillary sinus and wherein said squamous cell carcinoma is primary squamous cell carcinoma of the maxillary sinus.

3. The method of claim 1, wherein said squamous epithelial cells are oral squamous epithelial cells.

* * * * *